US011155776B2

(12) United States Patent
Parameswaran et al.

(10) Patent No.: US 11,155,776 B2
(45) Date of Patent: Oct. 26, 2021

(54) MEMBRANE BIOFILM REACTORS, SYSTEMS, AND METHODS FOR PRODUCING ORGANIC PRODUCTS

(71) Applicant: ARIZONA BOARD OF REGENTS ON BEHALF OF ARIZONA STATE UNIVERSITY, Scottsdale, AZ (US)

(72) Inventors: Prathap Parameswaran, Tempe, AZ (US); Rosa Krajmalnik-Brown, Chandler, AZ (US); Sudeep Popat, Chandler, AZ (US); Bruce Rittmann, Tempe, AZ (US); Cesar Torres, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 120 days.

(21) Appl. No.: 16/594,944

(22) Filed: Oct. 7, 2019

(65) Prior Publication Data
US 2020/0048596 A1    Feb. 13, 2020

Related U.S. Application Data

(62) Division of application No. 15/124,914, filed as application No. PCT/US2015/020000 on Mar. 11, 2015, now Pat. No. 10,435,659.

(Continued)

(51) Int. Cl.
*C12M 1/12*    (2006.01)
*C02F 3/10*    (2006.01)
(Continued)

(52) U.S. Cl.
CPC ............... *C12M 25/10* (2013.01); *B01D 3/10* (2013.01); *B01D 61/18* (2013.01); *B01D 63/04* (2013.01);
(Continued)

(58) Field of Classification Search
CPC ... C12M 25/10; C02F 1/66; C02F 1/02; C02F 3/34; C02F 3/102; C02F 3/208;
(Continued)

(56) References Cited

U.S. PATENT DOCUMENTS 4,758,341 A * 7/1988 Banner .................. B01D 53/22
                                                            210/232
6,387,262 B1   5/2002 Rittman et al.
(Continued)

FOREIGN PATENT DOCUMENTS

WO    2010008836 A2    1/2010
WO    2010045072 A2    4/2010
(Continued)

OTHER PUBLICATIONS

Abubackar H et al. "Biological conversion of carbon monoxide: rich syngas or waste gases to bioethanol." 2011. Biofuels, Bioproducts and Biorefining 5 (1), 93-114.
(Continued)

*Primary Examiner* — Michael L Hobbs
(74) *Attorney, Agent, or Firm* — Rodney J. Fuller; Booth Udall Fuller, PLC

(57) ABSTRACT

The present disclosure is directed toward membrane biofilm reactors primarily comprising microorganisms that produce chemical fuel products or precursors thereof. Reactors of the present disclosure can primarily comprise acetogens, a methanotrophs, and/or *Methanosarcina acetivorans*.

14 Claims, 7 Drawing Sheets

Related U.S. Application Data

(60) Provisional application No. 61/951,190, filed on Mar. 11, 2014.

(51) Int. Cl.

| | | |
|---|---|---|
| C02F 3/20 | (2006.01) | |
| C02F 3/34 | (2006.01) | |
| B01D 63/04 | (2006.01) | |
| B01D 61/18 | (2006.01) | |
| B01D 3/10 | (2006.01) | |
| C02F 1/02 | (2006.01) | |
| C02F 1/66 | (2006.01) | |
| C02F 3/12 | (2006.01) | |

(52) U.S. Cl.
CPC ............... *C02F 1/02* (2013.01); *C02F 1/66* (2013.01); *C02F 3/102* (2013.01); *C02F 3/208* (2013.01); *C02F 3/34* (2013.01); *B01D 2311/04* (2013.01); *B01D 2311/10* (2013.01); *B01D 2311/18* (2013.01); *B01D 2311/2661* (2013.01); *B01D 2311/2665* (2013.01); *B01D 2315/06* (2013.01); *B01D 2317/04* (2013.01); *C02F 3/1278* (2013.01); *C02F 2209/02* (2013.01); *C02F 2209/06* (2013.01); *Y02W 10/10* (2015.05)

(58) Field of Classification Search
CPC .......................... C02F 3/1278; C02F 2209/06; C02F 2209/02; B01D 3/10; B01D 61/18; B01D 61/04; B01D 2311/2665; B01D 2311/2661; B01D 2311/18; B01D 2311/10; B01D 2311/04; B01D 2317/04; B01D 2315/06; Y02W 10/15
See application file for complete search history.

(56) References Cited

U.S. PATENT DOCUMENTS

| | | | |
|---|---|---|---|
| 7,618,537 | B2 | 11/2009 | Bowman |
| 8,173,020 | B2 | 5/2012 | Bowman |
| 9,142,852 | B2 | 9/2015 | Rittman et al. |
| 9,216,919 | B2 | 12/2015 | Popat et al. |
| 10,385,304 | B2 | 8/2019 | Flory et al. |
| 10,563,162 | B2 | 2/2020 | Flory et al. |
| 2004/0229343 | A1 | 11/2004 | Husain et al. |
| 2009/0017514 | A1 | 1/2009 | Datta et al. |
| 2009/0095675 | A1* | 4/2009 | Runneboom ............ C02F 3/302 210/615 |
| 2009/0286296 | A1* | 11/2009 | Hickey ................. C12M 25/10 435/170 |
| 2010/0047886 | A1 | 2/2010 | Hickey et al. |
| 2011/0165667 | A1* | 7/2011 | Mets ..................... C25B 9/19 435/297.1 |
| 2011/0183390 | A1 | 7/2011 | Hickey et al. |
| 2011/0256597 | A1 | 10/2011 | Hickey et al. |
| 2011/0294177 | A1 | 12/2011 | Simpson et al. |
| 2012/0009638 | A1 | 1/2012 | Tsai et al. |
| 2012/0070888 | A1 | 3/2012 | Tsai et al. |
| 2012/0082869 | A1 | 4/2012 | Rittman et al. |
| 2013/0115684 | A1 | 5/2013 | Rittman et al. |
| 2014/0013658 | A1 | 1/2014 | Silverman et al. |
| 2014/0273143 | A1 | 9/2014 | Krajmalnik-Brown et al. |
| 2015/0030888 | A1 | 1/2015 | Popat et al. |

FOREIGN PATENT DOCUMENTS

| | | |
|---|---|---|
| WO | 2010117864 | 10/2010 |
| WO | 2011112540 A2 | 9/2011 |
| WO | 2013126450 A1 | 8/2013 |

OTHER PUBLICATIONS

Chen R et al. "Evolution of the microbial community of the biofilm in a methane-based membrane biofilm reactor reducing multiple electron acceptors." 2016. Environmental science and pollution research international, 23(10): 9540-9548.

Chung J et al. "Bioreduction of trichloroethene using a hydrogen-based membrane biofilm reactor." 2008. Environ. Sci. Technol. 42(2): 477-483.

Daniell J et al. "Commercial Biomass Syngas Fermentation." 2012. Energies, 5: 5372-5417.

Fennell D et al. "Methanotrophic attached-film reactor development and biofilm characteristics." 1992. Biotechnology and bioengineering, 40(10): 1218.

Hussain A et al. "Electricity generation from carbon monoxide and syngas in a microbial fuel cell." 2011. Applied Microbiology and Biotechnology 90 (3), 827-836.

International Search Report for application PCT/US2015/020000 filed on Mar. 11, 2015.

Latif H et al. "Trash to treasure: production of biofuels and commodity chemicals via syngas fermenting microorganisms." 2014. Current. Op. Biotechnol. 27: 79-87.

Martin K et al. "The membrane biofilm reactor (MBfR) for water and wastewater treatment: Principles, applications, and recent developments " 2012 Bioresource Technology 122: 83-94.

Merkey BV et al. "Modeling how soluble microbial products (SMP) support heterotrophic bacteria in autotroph-based biofilms." 2009. J. Theor. Biol. 259: 670-683.

Munasinghe P et al. "Biomass-derived syngas fermentation into biofuels: Opportunities and challenges." 2010. Biores Technol. 101(13): 5013-5022.

Paulson LD. New Biofilm technology promising for wastewater treatment. Website: http://www.rwlwater.com/promising-biofilm-technology-for-wastewater-treatment/ Downloaded on Jul. 11, 2013.

Perez J et al. "Biocatalytic reduction of short-chain carboxylic acids into their corresponding alcohols with syngas fermentation." 2013. Biotechnol. Bioeng.110(4): 1066-1077.

Quereshi N et al. "Biofilm reactors for industrial bioconversion processes: employing potential of enhanced reaction rates." 2005. Microb. Cell Factories 4:24, 1-21.

Rittmann B. "The membrane biofilm reactor is a versatile platform for water and wastewater treatment." 2007. Environmental Engineering Research 12(4): 157-175.

Sahinkaya E et al. "Performance of a sulfide-oxidizing, sulfur-producing membrane biofilm reactor treating sulfide-containing bioreactor effluent." 2011. Environmental Science & Technology 45(9): 4080-4087.

Shen Y et al. "Enhancing mass transfer and ethanol production in syngas fermentation of Clostridium carboxidivorans P7 through a monolithic biofilm reactor." 2014. Applied Energy, 136: 68-76.

Shen Y et al. "Syngas fermentation of Clostridium carboxidivoran P7 in a hollow fiber membrane biofilm reactor: Evaluating the mass transfer coefficient and ethanol production performance." 2014. Biochemical Engineering Journal, 85: 21-29.

Sipma J et al. "Carbon momoxide conversion by anaerobic bioreactor sludges." 2003. FEMS Microbial Ecology. 44: 271-277.

Steinbusch K et al. "Alcohol production through volatile fatty acids reduction with hydrogen as electron donor by mixed cultures." 2008. Water Research 42(15): 4059-4066.

Steinbusch K et al. "Biological formation of caproate and caprylate from acetate: fuel and chemical production from low grade biomass." 2011. Energy & Environmental Science 4(1): 216-224.

Sun F et al. "Aerobic methane oxidation coupled to denitrification in a membrane biofilm reactor: Treatment performance and the effect of oxygen ventilation." 2013. Bioresource Technology, 145:2-9.

Tang Y et al. "Hydrogen permeability of the hollow fibers used in H2-based membrane biofilm reactors." 2012. J Membr. Sci. 407-408: 176-183.

Van Ginkel S et al. "Kinetics of nitrate and perchlorate reduction in ion-exchange brine using the membrane biofilm reactor (MBfR)." 2008. Water Research 42 (15): 4197-4205.

(56) References Cited

OTHER PUBLICATIONS

Van Houten RT et al. "Biological sulphate reduction using synthesis gas as energy and carbon source." 1996. Biotechnol. Bioeng. 50: 136-144.

Vane L et al. "Membrane-assisted vapor stripping: energy efficient hybrid distillation-vapor permeation process for alcohol-water separation." 2008. J Chem Bioechem Technol 83(9): 1275-1287.

Vega J et al. "Study of Gaseous Substrate Fermentations: Carbon Monoxide Conversion to Acetate. 2. Continuous Culture." 1989. Biotechnol. Bioeng. 34: 785-793.

Xin J et al. "Continuous biocatalytic synthesis of epoxypropane using a biofilm reactor." 2003. Process Biochemistry, 38(12): 1739-1746.

Xu D et al. "Syngas fermentation to biofuels: effects of ammonia impurity raw syngas on hydrogenase activity." 2012. Biomass & Bioenergy 45: 303-310.

Zhang F et al. "Fatty acids production from hydrogen and carbon dioxide by mixed culture in the membrane biofilm reactor" Water Research, 2013, 47: 6122-6129.

Ziv-El M et al. "Managing methanogens and homoacetogens to promote reductive dechlorination of trichloroethene with direct delivery of H2 in a membrane biofilm reactor." 2012. Biotechnol. Bioeng. 109(9): 2200-2210.

\* cited by examiner

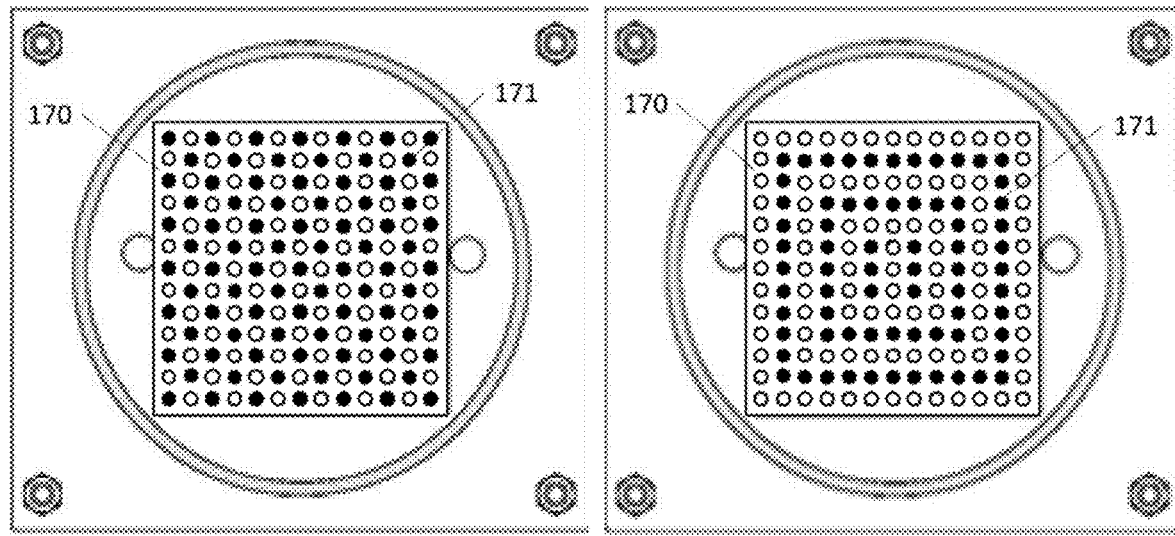
FIG. 5A
FIG. 5B
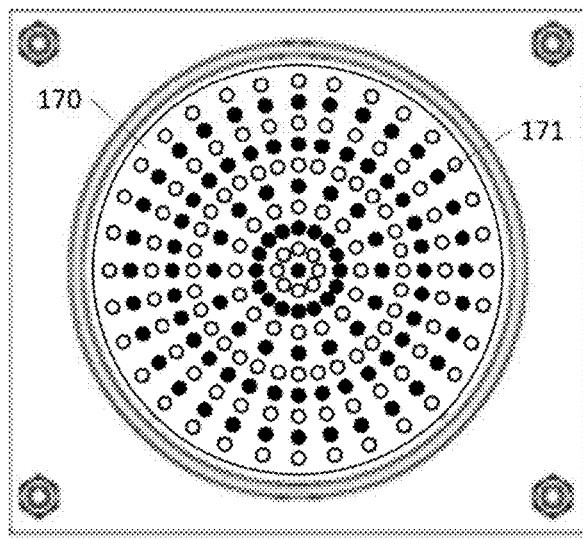
FIG. 5C

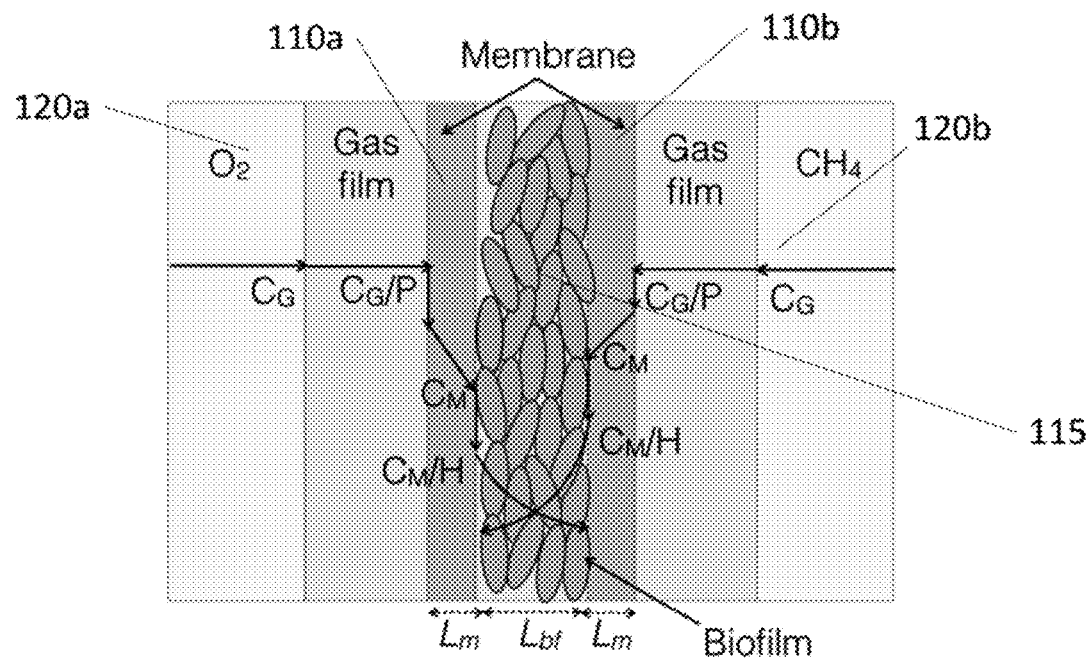
FIG. 5D(i)
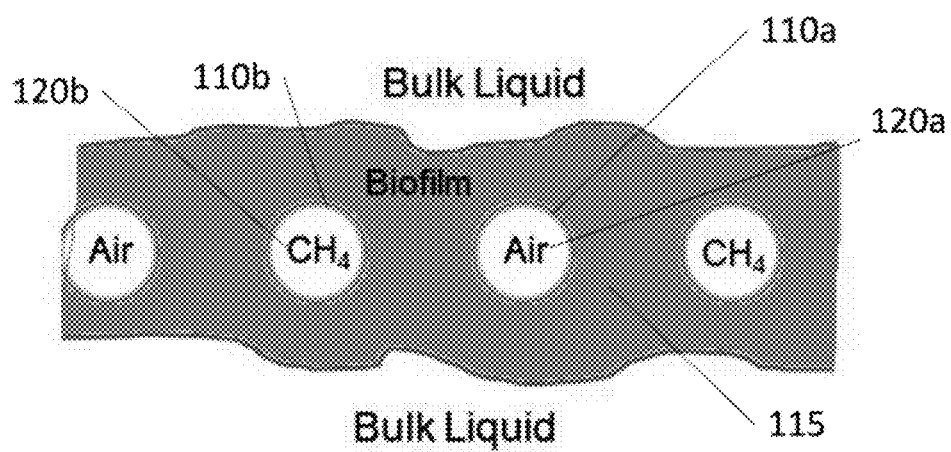
FIG. 5D(ii)

MEMBRANE BIOFILM REACTORS, SYSTEMS, AND METHODS FOR PRODUCING ORGANIC PRODUCTS

CROSS-REFERENCE TO RELATED APPLICATIONS

This application is a divisional of U.S. patent application Ser. No. 15/124,914, filed on Sep. 9, 2016 (issued as U.S. Pat. No. 10,435,659), which is the U.S. National Stage of International Application No. PCT/US2015/020000, filed on Mar. 11, 2015, which claims the benefit of and priority to U.S. Provisional Application No. 61/951,190 filed on Mar. 11, 2014, the contents of each of which is hereby incorporated by reference in their entireties.

FIELD OF THE INVENTION

The invention relates to biological conversion of electron and/or carbon dense gaseous feedstock to organic products in membrane biofilm reactors.

BACKGROUND

The high costs of petroleum, along with the increasing harmful environmental effects due to its use, have led researchers to search for renewable sources of energy and fuels. Up to now, established renewable energy sources, such as wind turbines and solar photovoltaics, focus on the production of electrical energy. Since as much as 30% of all energy consumption is in the form of liquid transportation fuels, a need exists to produce liquid fuels in a renewable way (US Energy Information Administration, 2011).

The chemical complexity of liquid fuels (e.g., ethanol or higher organic alcohols and alkanes) demands using sets of complex catalysis reactions that are best achieved through microbial enzymatic processes. The precursors of these liquid fuels could be simple gases, including hydrogen ($H_2$), methane ($CH_4$), or syngas ($CO/H_2/CO_2$), or any combination of the above gases (including $CO/H_2$ or $CO_2/H_2$). Among the gases, $H_2$ could become an important precursor to liquid fuels, because it can be produced from water electrolysis, for which the electrical power can be derived from renewable sources or from biomass, which is inherently renewable. $CH_4$ is of especially high interest because it has become readily available from hydraulic fracturing and can be produced by fermentation of biomass.

Acetogens comprise a unique group of anaerobic bacteria that utilize the Wood-Ljungdahl pathway to convert $H_2/CO_2$, syngas ($H_2/CO$) and a variety of sugars to produce predominantly acetate, along with the versatility to produce ethanol, butanol and other higher acids and alcohols through fermentative pathways (Drake, 1994). Acetogens have been employed for production of valuable chemicals from gaseous substrates at a commercial scale (Munasinghe and Khanal, 2010; Latif et al, 2014). Table 1 provides a selective list of acetogens able to utilize syngas, along with their titer values of the respective chemical end product, including current industrial potential.

TABLE 1

Microbiological capabilities of various mesophilic pure strains of acetogenic bacteria using syngas ($H_2 + CO_2/H_2 + CO$) to produce value added chemicals.

| Organism | Primary metabolic products | Conc. (g L$^{-1}$) | Temp. (° C.) | pH profile | Observations |
| --- | --- | --- | --- | --- | --- |
| Acetobacterium woodii | Acetate | 44 | 30 | 6.2 | Not capable of generating other products |
| Clostridium ljungdahlii | Ethanol, acetate, butyrate | 48 (ethanol) | 37 | 5.8 | Maximum ethanol capacity 100 gallons per dry ton of waste biomass |
| Clostridium ragsdalei | Ethanol, acetate | 25.26 (ethanol) | 32-37 | 6.1 | Severe limitation for ethanol production below pH 6 |
| Clostridium coskatii | Ethanol, acetate | 28 (ethanol) 12.5 (acetate) | 37 | 5.2 | Gas transfer in suspension reactors limited due to lower $K_La$ of gas transfer |
| Clostridium autoethanogenum | Ethanol | 0.26-0.32 | 37 | 6.4 | Lack of specificity with 2,3 butanediol and butanol produced in large quantities |
| Acetobacterium bacchi | Ethanol | 1.7 | 37 | 7.7-8 | Only alkaliphilic strain but with limited capacity |
| Moorella thermoacetica | Acetate | 7.1 | 60 | 6.4 | Limited capability to produce significant acetate from H2/CO |
| Thermoanaero-bacter kivui | Ethanol, acetate | 21 mol ethanol/mol acetate | 60 | 6.6 | 3:1 stoichiometry for CO:ethanol |

Acetogens that are capable of using $H_2/CO_2$ or syngas belong to two categories: mesophilic (32-37° C.) and thermophilic (55-60° C.). While most studies have focused on unearthing the capabilities of mesophilic acetogens, several thermophilic acetogens, such as *Thermoanaerobacter kivui* and *Moorella thermoautotrophica*, have promise due to their high metabolic rates and capabilities.

Several challenges, however, limit the commercial application of acetogenic bacteria. For instance, higher gas-liquid mass transfer rates are needed. Gas-based metabolism by acetogens involves the utilization of relatively insoluble $H_2$ and $CO/CO_2$ for product synthesis, and a significant quantity of the gas is required to satisfy stoichiometric requirements. Stoichiometry indicates that the reactant gas requirements depend upon the nature of the specific microbial reaction, as indicated below for acetate and ethanol.

Acetate Production:

$$4CO+2H_2O \rightarrow 4CH_3COOH+2CO_2 \qquad (1)$$

$$2CO_2+4H_2 \rightarrow 4CH_3COOH+2H_2O \qquad (2)$$

Ethanol Production:

$$6CO+3H_2O \rightarrow 4C_2H_5OH+4CO_2 \qquad (3)$$

$$2CO_2+6H_2 \rightarrow 4C_2H_5OH+3H_2O \qquad (4)$$

High-efficiency gas transfer to the acetogens is essential, since $H_2$ and CO are very low-solubility gases. However, conventional designs to provide the highest volumetric gas transfer rates are not necessarily effective due to the significant energy consumption.

In addition to higher-efficiency gas transfer, achieving higher catalyst (active biomass) concentrations is also needed. Though it is preferable to have most of the carbon go to products rather than biomass, a certain cell concentration is needed to sustain industrially relevant production rates. Conventional suspended-cell recycling strategies using semi-permeable membranes have been plagued by fouling problems (Quereshi et al., 2005).

Methanotrophs represent another class of microorganisms that oxidize methane predominantly to $CO_2$. However, under certain conditions such as nutrient limitation, these microorganisms store excess carbon and electrons in storage products such as polyhydroxybutytrate (PHB), which is a precursor to commercial plastics. These methanotrophs could also be metabolically engineered to produce alcohols and fatty acids too.

Process challenges when employing methanotrophs have been identified by the inventors and relate to the nature of the feed gases and delivery of such gases to a biofilm reactor. When employing methanotrophs, the mixture of the two gases required for their metabolism is $CH_4$ and $O_2$. Both gases are relatively insoluble in water (~40 mg $O_2$/L and 23 mg $CH_4$/L at STP), making it difficult to dissolve either at high rates. In addition, practical biofuel applications will most likely obtain $O_2$ from air, which has ~20% $O_2$ by volume, decreasing the solubility by a factor of 5. The use of air also brings an inert gas into the mixture, $N_2$, which dilutes the reactants.

Another complication of using $CH_4$ and $O_2$ together is the flammability of this gas mixture. $CH_4$ has a lower flammability limit (LFL) of 5% and a higher flammability limit (HFL) of 15% in air. If mixing these gases before delivering them to methanotrophs, the mixture should be either below the LFL or above the HFL to avoid the risk of combustion. Based on the stoichiometry of the reaction carried out by methanotrophs (shown below), an optimal mixture in air would be ~9% $CH_4$ balanced by air (~18% $O_2$), a flammable mixture.

$$CH_4+2O_2+2H_2O \rightarrow CO_2+4H_2O \qquad (5)$$

In order to achieve a non-flammable mixture, one approach would be to operate below the LFL of 5% $CH_4$. This approach, however, introduces several serious drawbacks. First, the low concentration of $CH_4$ in the gas significantly decreases its flux across the hollow fiber, which slows the overall reaction rate. Second, the addition of air creates a requirement for gas exhaust (mostly $N_2$) from the system. The $CH_4$ concentration of this exhaust gas would ideally be almost zero to minimize $CH_4$ emissions and maximize $CH_4$ utilization. However, this also implies that at least part of the reactor will encounter a very low $CH_4$ concentration.

The challenges outlined above not only apply to acetogens and methanotrophs, but to any microbial metabolism that is based on feeding a gaseous substrate. New reactor configurations addressing these challenges should be considered for commercializing microbially driven gas fermentations/biotransformations. Other microorganisms able to use gaseous substrates aside from acetogens should also be considered.

SUMMARY OF THE INVENTION

The present application focuses on a technology to deliver gaseous feedstock directly to microbial biofilms with high active biomass concentrations capable of organic biochemical production. Such biofilm processes offer an effective means for achieving the required cell concentrations and gas-transfer rates, along with an inherent benefit of increased tolerance to inhibitors in the feed gas stream.

One aspect of the present disclosure relates to a membrane biofilm reactor comprising a vessel defining a volume; a hollow fiber membrane defining an outer surface and a lumen, the hollow fiber membrane being disposed within the volume; and a biofilm formed on the outer surface of the hollow fiber membrane comprising at least a majority of at least one of the following microorganisms: acetogens, methanotrophs, and *Methanosarcina acetivorans*. In various embodiments, the biofilm consists essentially of microorganisms that produce a metabolic byproduct of at least one of the following: an alkane, organic acid, aldehyde, an alcohol, or a polyhydroxyalkanoate. In various embodiments, a first plurality of hollow fiber membranes, each comprising a lumen; a first gas feedstock provided through an inlet in fluid communication with the lumens of the first plurality of hollow fiber membranes; a second plurality of hollow fiber membranes, each comprising a lumen; and a second gas feedstock provided through an inlet in fluid communication with the lumens of the second plurality hollow fiber membranes, wherein the first gas feedstock is different from the second gas feedstock.

Similarly, another aspect of the disclosure relates to a membrane biofilm reactor comprising a vessel defining a volume; a hollow fiber membrane defining an outer surface and a lumen, the hollow fiber membrane being disposed within the volume containing an aqueous medium; and a biofilm formed on the outer surface of the hollow fiber membrane consisting essentially of thermophilic microorganisms, wherein the temperature of the aqueous medium is about 50° C. to about 70° C. or about 55° C. to about 60° C.

Further aspects of the present disclosure relate to a bioreactor system for producing and extracting organic compounds comprising a membrane biofilm reactor comprising a hollow fiber membrane having an outer surface; a biofilm disposed on the outer surface of the hollow fiber membrane; an aqueous bath; and a separation unit configured to extract organic compounds from the aqueous medium. In various embodiments, the bioreactor system can further comprise a heater configured to heat the aqueous medium to a temperature of about 50° C. to about 70° C. or about 55° C. to about 60° C.

Another aspect of the present disclosure relates to a method of producing and extracting at least one of an alkane, an organic acid, an alcohol, or a polyhydroxyalkanoate by providing a C-1 feedstock to a membrane biofilm reactor comprising a biofilm disposed on a hollow fiber membrane disposed in an aqueous medium and extracting at least one of an alkane, an organic acid, or an alcohol from the aqueous medium.

Embodiments of the present disclosure can also be used to cultivate and identify microorganisms that are capable of forming a biofilm under selected conditions. A method of developing a biofilm can comprise: providing a membrane biofilm reactor comprising at least one hollow fiber membrane disposed within a vessel in an aqueous bath, wherein the hollow fiber membrane comprises an outer surface and a lumen extending along at least a portion of the length of the fiber; adding a source of unidentified microorganisms into the aqueous bath; and providing a C-1 feedstock though a lumen of the hollow fiber membrane, thereby causing a biofilm to form on the outer surface of the membrane.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

FIGS. 5A-5C illustrate a schematic of a gas outlet pattern of a membrane module wherein a first gaseous feedstock composition is delivered to a hollow fiber membrane through the outlets represented by the black circles and a different gaseous feedstock composition is delivered to the outlets represented by the white circles.

FIGS. 5D(i) and 5D(ii) illustrate a schematic of a cross-section of a hollow fiber membrane with a biofilm formed on the outer surface thereof.

DETAILED DESCRIPTION OF THE INVENTION

Figure 1:
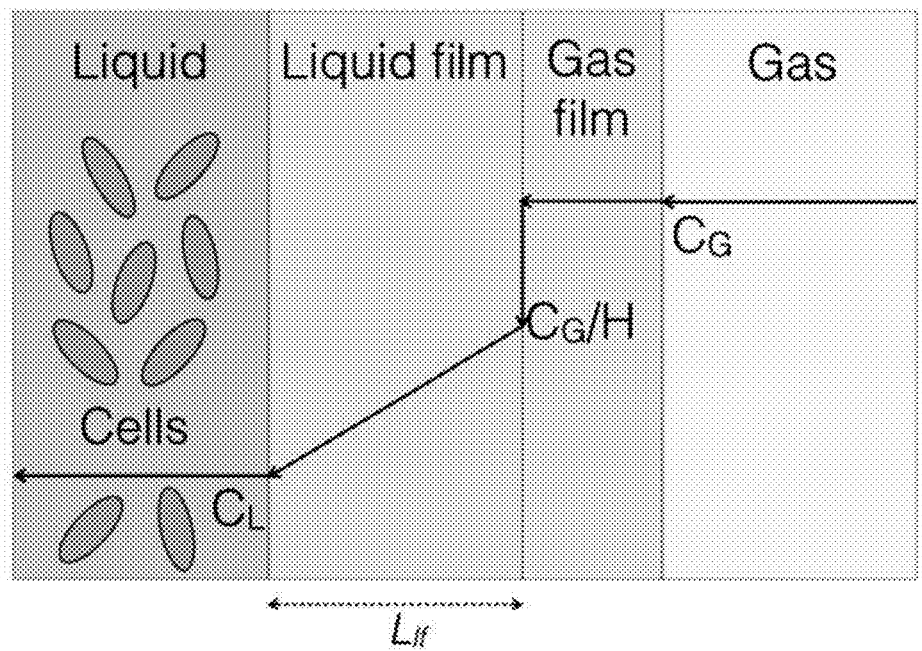
FIG. 1 illustrates a schematic showing gas transfer in conventional bubbled systems.

A Membrane Biofilm Reactor (MBfR) employs efficient, direct supply of gaseous substrates to microorganisms that form a biofilm on the outside of a gas-transfer membrane (see e.g., U.S. Pat. Nos. 6,387,262 and 7,618,537 incorporated by reference in their entirety). Major increases in the overall membrane volumetric mass transfer coefficient ($K_L a$) can be achieved through MBfRs. Direct delivery of a gaseous feedstock to a biofilm results in a reaction zone that has a continuous supply of the gaseous substrates without a diffusion limitation arising from a liquid film that forms in all bubbled gas transfer systems, such as CSTRs (compare, e.g., FIGS. 1 to 2). In an MBfR, the liquid film is replaced by the membrane wall; thus, as long as the resistance to mass transfer in membrane is lower than through a liquid film in a conventional system (i.e. $1/Hk_M$ is lower than $1/k_L$), higher gas delivery rates will result.

In accordance with the present invention, an MBfR is utilized to produce organic products, such as organic acids, polyhydroxyalkanoates, alcohols, and alkanes. The organic products are the metabolic byproducts of the microorganisms supported in the MBfR. These products can be utilized as liquid fuel or precursors to liquid fuels or other industrial chemical feedstocks. In some embodiments, the metabolic byproduct can be at least one of the following: methanol, ethanol, propanol, n-butanol, n-hexanol, formaldehyde, formic acid, acetic acid, lactic acid, succinic acid, butyric acid, or any combination thereof. Using an MBfR to achieve high-rate liquid biofuel production is a novel strategy that is targeted to overcoming the challenges of using gaseous substrates. Delivering gaseous feedstock or a combination of gaseous feedstock directly to a microbial biofilm MBfR provides superior gas transfer, even though all of the gases have very low water solubility.

Figure 2:
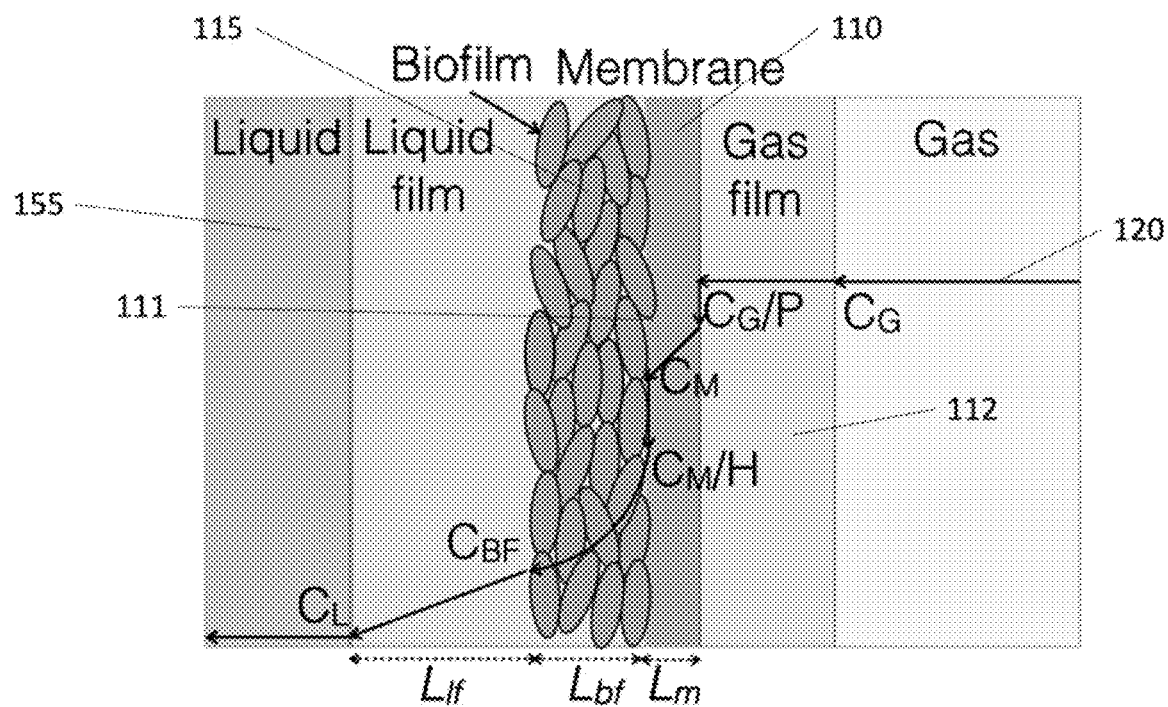
FIG. 2 illustrates a schematic of a cross-section of a hollow-fiber membrane with a biofilm formed on the outer surface thereof, a liquid medium surrounding the biofilm, and gaseous feedstock delivered through the hollow fiber membrane to the biofilm.
Figure 3:
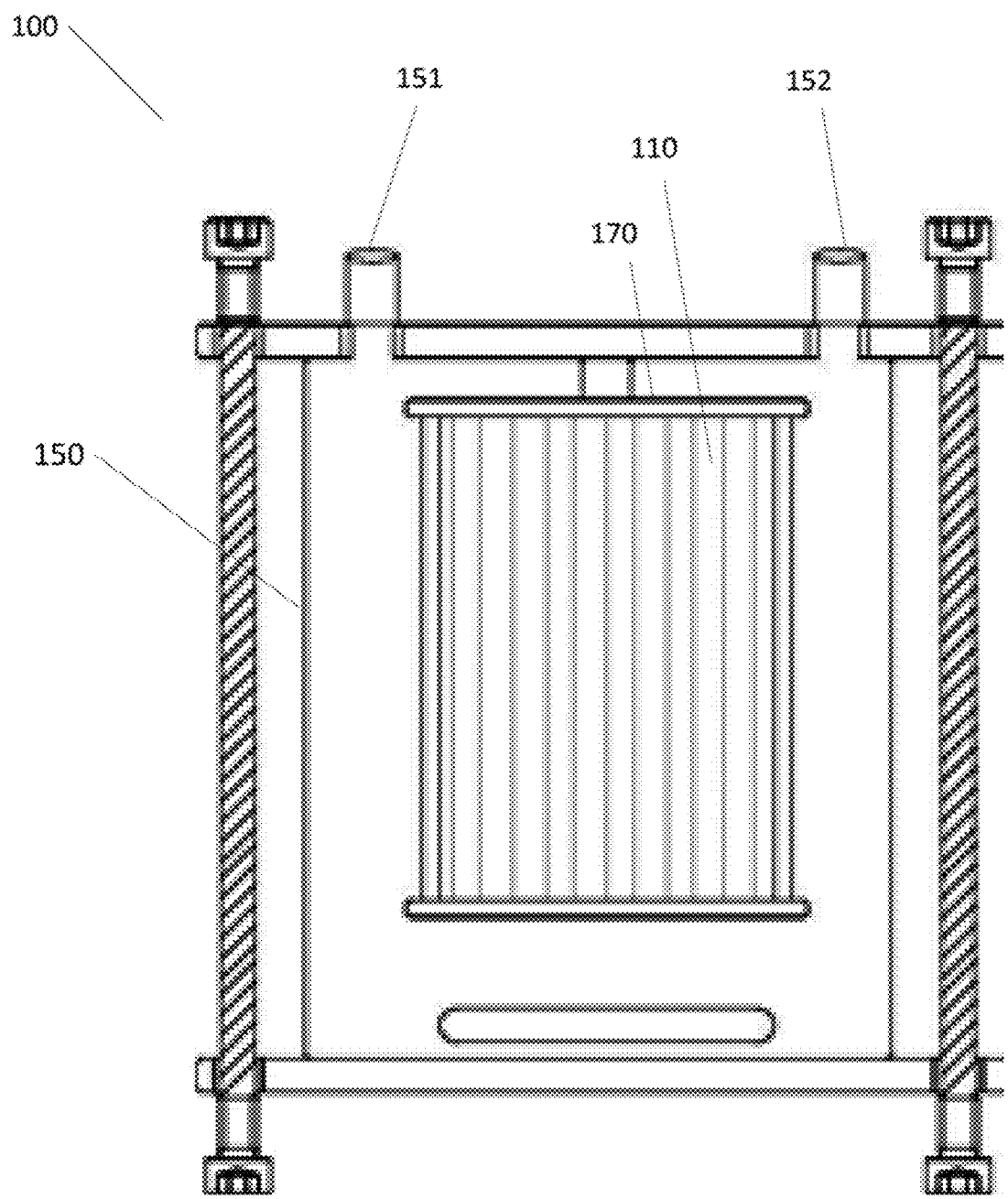
FIG. 3 illustrates a schematic of a membrane biofilm reactor.

FIG. 2 schematically shows a cross-section of a hollow fiber membrane 110 with a biofilm layer 115 developed on the outer surface 111 of the membrane. FIG. 3 provides a schematic illustration of a MBfR 100 for providing gaseous feedstock for an active biofilm 115 consisting essentially of microorganisms that produce desired metabolic byproducts. Microorgansims that are suitable for the production of organic products include acetogens (including some homoacetogens), methanotrophs, and the methanogen, *Methanosarcina acetivorans*. These microorganisms have capabilities to convert gaseous substrates to value added chemical fuels, as shown in Table 2.

TABLE 2

Examples of microorganisms that utilize gaseous substrates to produce valuable chemical products

| Microorganism category | Gases utilized | Chemical products formed |
|---|---|---|
| Acetogens | $H_2$, $CO_2$, CO | Organic acids, alcohols |
| Methanotrophs | $CH_4$, $O_2$ (aerobic members) | Methanol, Formaldehyde, polyhydroxybutyrate |
| *Methanosarcina acetivorans* | CO | Acetate, formate, some methane |

A majority of biofilm 115 can comprise or biofilm 115 can consist essentially of acetogens, methanotrophs, *Methanosarcina acetivorans*, or a combination thereof. In some embodiments, biofilm 115 can consist essentially of a pure or mixed culture—such as *Clostridium ragsdalei, Butyrib-* acterium methylotrophicum, *Clostridium ljungdahlii, Clostridium carboxidivorans, Acetobacterium woodii, Clostridium coskatii, Clostridium autoethanogenum, Acetobacterium bacchi, Methanosarcina acetivorans, Moorella thermoacetica, Thermoanaerobacter kivui, Methylosinus trichosporium* (particularly, the OB3b strain), or combinations thereof—which can generate the organic products from the gaseous feedstock, depending on the gaseous stock and culture selected. Those skilled in the art will appreciate that numerous combinations of gaseous feedstock and culture can be selected as desired for generating a particular liquid product desired. In addition, in some embodiments, other microorganisms, which are not associated with the bioproduction of organic products, can be present in a smaller percentage to facilitate a healthy ecology for efficient production of organic products, and these can include heterotrophic homoacetogens, such as from the *Clostridium* genera and *Spirochaetes, Chlorojlexi phyla*. MBfR 100 can comprise biofilm 115 that amounts to at least 2 g/L of vessel, 5 g/L of vessel, 10 g/L of vessel, 20 g/L of vessel, 25 g/L of vessel, 30 g/L of vessel, or more, or any range there between.

The interface between biofilm 115 and membrane 110 keeps the liquid and gas phases separated from each other. As shown in FIG. 2, gaseous components 120 enter the system as gas stream and flow into a lumen 112 between a surrounding membrane wall. The gaseous feedstock diffuses through membrane 110 for consumption by the microbes in biofilm 115 that adhere to outer surface 111. Similarly, in lieu of a hollow fiber membrane configuration, a flat sheet membrane sealed and connected along the perimeter to another flat sheet membrane to form central space can also be used.

With reference to FIG. 3, MBfR 100 can comprise a vessel 150 defining a volume and a plurality of hollow fiber membrane elements 110 disposed within the volume. The plurality of hollow fiber membranes 110 are coupled to one or more modules 170 defining at least one gas inlet and at least one conduit for delivering the gaseous substrate to lumen 112 of membranes 110. Vessel 150 surrounds the plurality of membrane elements 110 in MBfR 100 and retains an aqueous medium 120 for growth and maintenance of biofilm 115 on the outer surface of membrane 110.

In some embodiments, medium 120 can be pressurized to increase the process gas transfer rate through the hollow fiber walls. In one embodiment, the membrane lumen is pressurized in the range of 2 to 1250 psig. Vessel 150 can be configured to a pressure vessel. Such vessels can be made of fiber reinforced plastic (FRP) composite materials for maximum operating pressures ranging from 150 psig to 1250 psig. Vessel 150 can comprise any suitable dimension to facilitate efficient production of the desired metabolic byproduct. In some embodiments, vessel 150 is configured to control temperature and pH of medium 120, which contains nutrients needed to sustain the activity of the microbial cells. Medium 120 can be stirred to provide adequate mixing and sparged with a suitable gas, if necessary, to maintain a suitable aqueous environment. A re-circulating liquid conduit 125, 126 can re-circulate medium 120 through vessel 150. To facilitate extraction of the metabolic byproducts, with reference to FIGS. 4A and 4B, medium 120 can flow from vessel 150 through outlet 151 into conduit 125 to a separation unit 130 to recover metabolic byproducts. Conduit 126 can return the remaining medium 120 from unit 130 to vessel 150 via inlet 152 with the aid of a pump at rate recorded by a flow meter. Separation unit 130 removes the desirable organic product from medium 120, while leaving a majority of the water and residual nutrients in the remaining medium 120. In some embodiments, a nutrient feed conduit 127 is connected to conduit 126 or vessel 150 to compensate for the amount of water removed and to replenish nutrients as needed. A mixing unit 160 can facilitate mixing and/or testing of returning medium 120 to vessel 150.

The flow rates of medium 120 recirculated can be selected so that there is no significant liquid boundary layer that impedes mass transfer near the liquid-facing side of the membrane and there is no excessive shear that may severely limit the attachment and/or formation of biofilm 115 on membrane surface 111. The superficial linear velocity of the liquid tangential to the membrane should be in the range of 0.01 to 20 cm/s and preferably 0.05 to 5 cm/s. In addition to the liquid linear velocity, the thickness of biofilm 115 can be controlled by other means to create shear on the liquid-biofilm interface, including scouring of the external membrane surface with gas bubbles and free movement of the hollow fibers. Also, operating conditions that affect the metabolic activity of the microbial cells and the mass transfer rates of gases and nutrients can be manipulated to control the thickness of biofilm 115. The thickness of biofilm 115 can be in the range of 1-500 µm, preferably 5-200 µm.

Upon the utilization of gaseous feedstock delivered through membrane, a gradient for their transport from the gas feed side is created due to biochemical reaction on the membrane liquid interface. This reaction creates liquid-fuel or chemical feedstock that diffuses into the liquid circulating past the biofilm. Thus, the very large surface areas of the membrane pores are usable for gas transfer to the biofilm and the product is recovered from the liquid side.

Depending on the nature of the desired product, a number of technologies can be used for product recovery. For example, distillation (such a vacuum or fractional distillation), dephlegmation, pervaporation, and liquid-liquid extraction can be used for the recovery of alkanes and organic alcohols, such as methanol, ethanol, n-butanol, and the like, whereas electrodialysis and ion-exchange can be used for the recovery of organic acids in ionic form, such as acetate, butyrate, and other ionic products. In some embodiments, wherein the reactor is operated at elevated temperatures, a vacuum distillation column 130 can be connected to vessel 150, as illustrated in FIG. 4B.

Figure 4A:
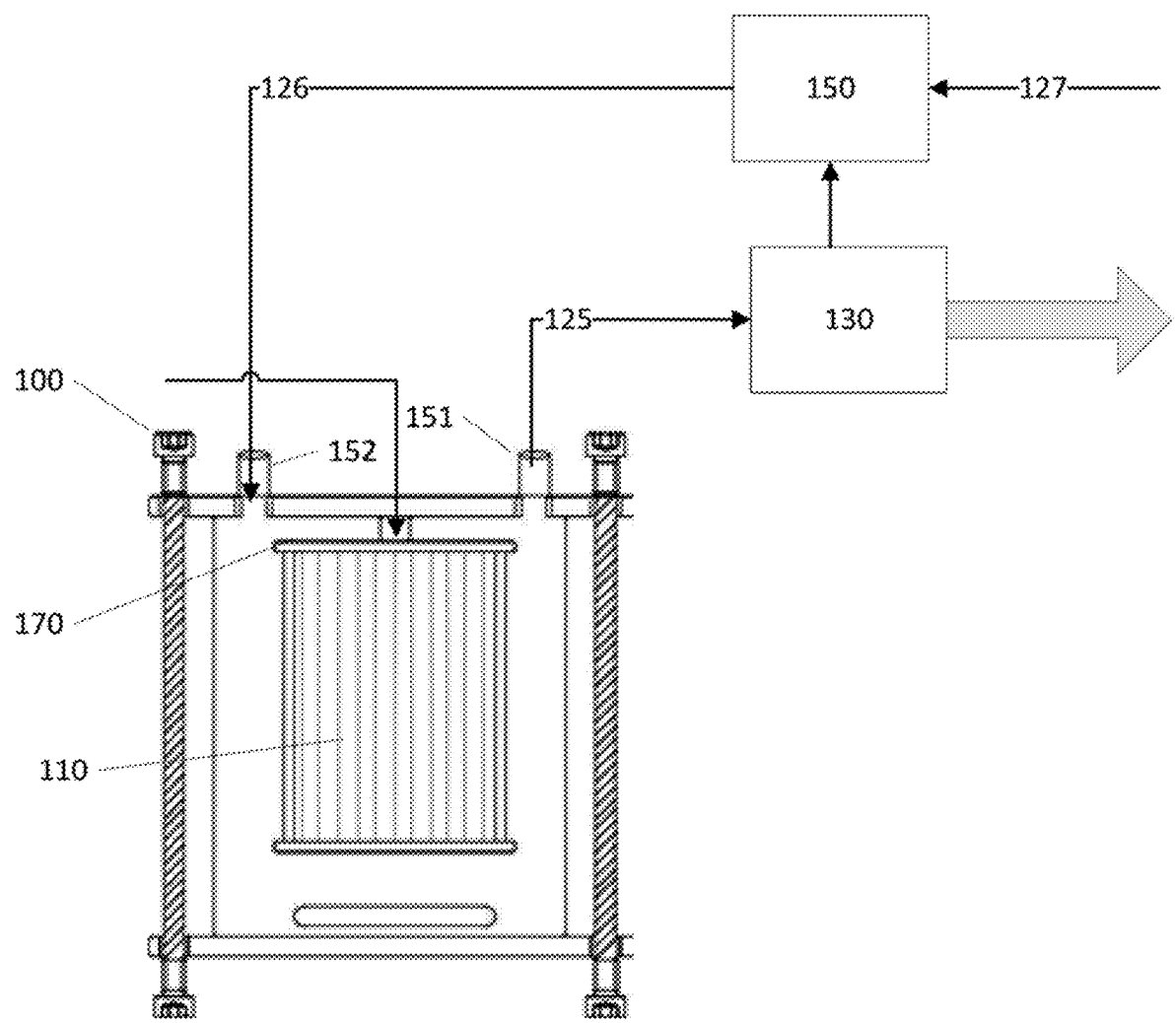
FIG. 4A illustrates a schematic of a membrane biofilm reactor and a separation unit with a circulation loop connecting the reactor to the separation unit.
Figure 4B:
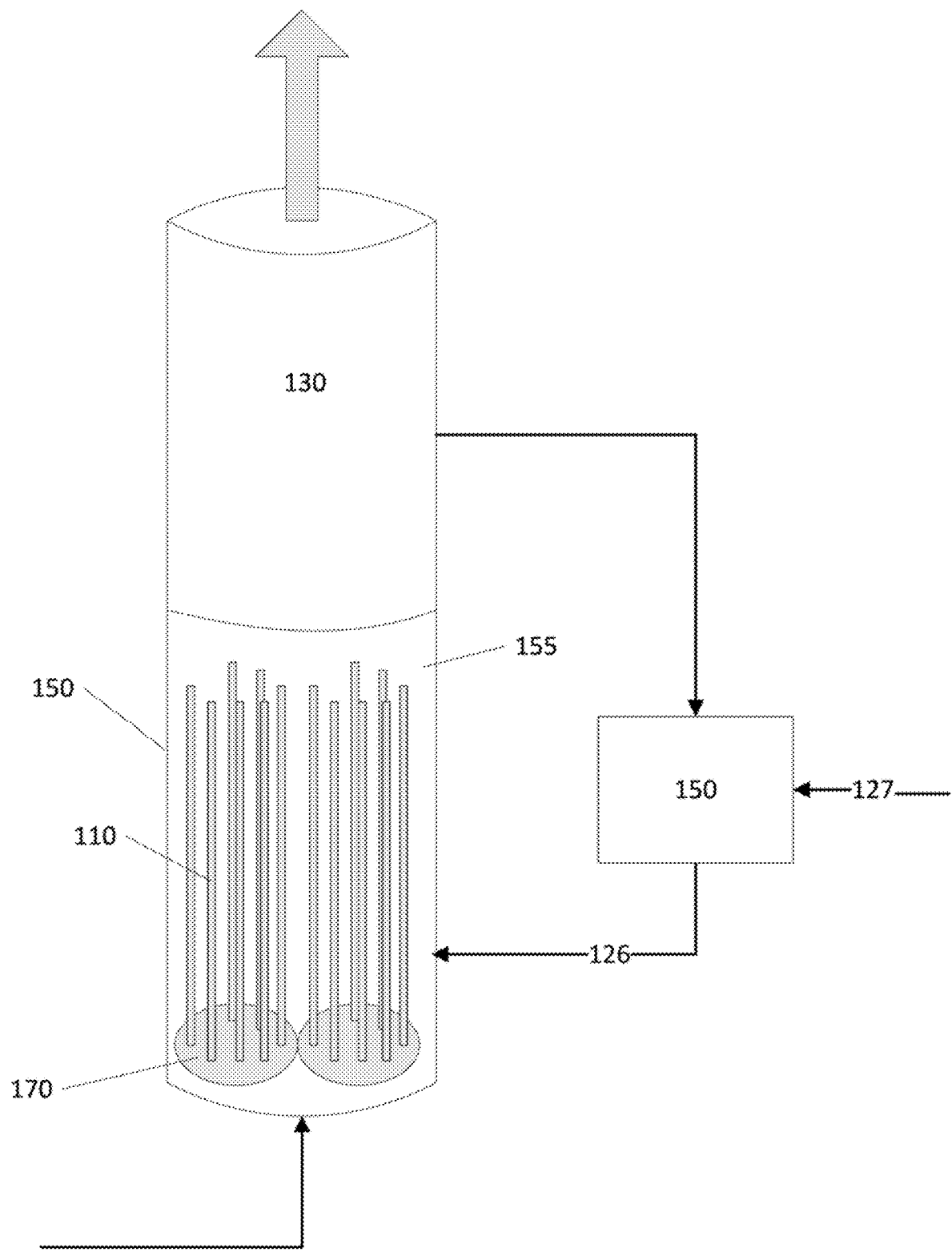
FIG. 4B illustrates a schematic of a membrane biofilm reactor and a vacuum distillation column disposed above vessel.

The membranes can be configured into typical modules 170 as shown in FIGS. 4A-4B for hollow fibers 110. The gas flows into the fine fibers that are bundled and potted inside a shell through which the gaseous feedstock is distributed to the lumen of the fibers 110. Very high surface area gaseous distribution in the range of 1000 $m^2$ to 5000 $m^2$ per $m^3$ of the reactor can be achieved with such modules. The gaseous substrate fed into the lumen of hollow fiber membrane 110 passes to biofilm disposed on the outer surface of hollow fibers. In this manner, gaseous substrates are converted into a liquid product that mixes with the aqueous medium.

In some embodiments, C-1 gases are provided to the biofilm, i.e., $CH_4$, CO, and/or $CO_2$. In further embodiments, depending on the type of microorganism, inorganic gases, such as $H_2$, $O_2$, and $N_2$, also can be delivered to the biofilm. Table 2 provides examples of gaseous components that can be provided to a biofilm. In some embodiments, the gas feedstock comprises one of the following % mixtures: 75-85:15-25 of $H_2$ and $CO_2$, 55-65:25-35:5-15 of $H_2$, CO, and $CO_2$, 15-21:21-27:3-9:45-60 of $H_2$, CO, $CO_2$, and $N_2$; and 5-15:5-15:70-90 of $CH_4$, $O_2$, and $N_2$. In some embodiments, the feedstock components are fed through the lumen of the hollow fiber membrane as a mixture. In other embodiments, the feedstock components are fed to separate and distinct membranes. Delivering separately can reduce risk of combustion, as the case would be with a combined mixture of $CH_4$ and $O_2$.

To facilitate delivery of feedstock components to separate and distinct membranes, the shell of the membrane module is configured to comprise at least two gas inlets and at least two distinct gas conduits, each of which are in fluid communication with the lumens of a separate plurality of membranes. The two gas conduits can branch to deliver respective feedstock components through gas outlets 171 to the plurality of hollow fiber membranes 110 in a certain pattern (e.g., as shown in FIGS. 5A-5C) and a particular spacing to ensure delivery of the different gaseous compositions to a biofilm 115 that is sandwiched between two neighboring hollow fiber elements 110 (e.g., as shown in FIGS. 5D(i) and 5D(ii)). For example, a hollow fiber membranes 110a receiving one gaseous composition 120a will have at least one neighboring hollow fiber membrane 110b receiving a different gaseous composition 120b. The distance between these two membranes 110a, 110b is such that biofilm 115 forms between them and receives gaseous feedstock from both. In some embodiments, the spacing between the neighboring membranes is less than 600 μm, less than 500 μm, less than 400 μm, or less than 100 μm.

For example, again with reference to FIGS. 5D(i) and (ii), an MBfR can be configured to supply air 120a and $CH_4$ 120b in separate, alternating fibers 110a, 110b that are placed in sufficiently close proximity to each other. By separating the two gases 120a, 120b, a high concentration of both reactants in each fiber can be obtained. In addition, pure $CH_4$ in one set of fibers and air in the other set of fibers can continuously flow through the respective hollow fibers at a rate that does not deplete the $O_2$ concentration significantly. The high gas concentrations can translate into high fluxes, e.g., up to 20 times higher compared to a gas mix approach. In various embodiments, one type of hollow fiber 120a can be placed in close proximity (e.g., <500 μm) to the other type 120b to ensure that biofilm 115 grows in between the two types 120a, 120b. Counter diffusion of $CH_4$ and $O_2$ can occur within biofilm 115, where the gases can be quickly consumed. Because this configuration mixes the gases inside biofilm 115 (which contains mainly water), no explosive gas mixture is formed. Furthermore, $CH_4$ off-gassing is minimized. Balancing the fluxes between the two streams can be achieved by controlling the gas pressure to each type of fiber.

Figure 6:
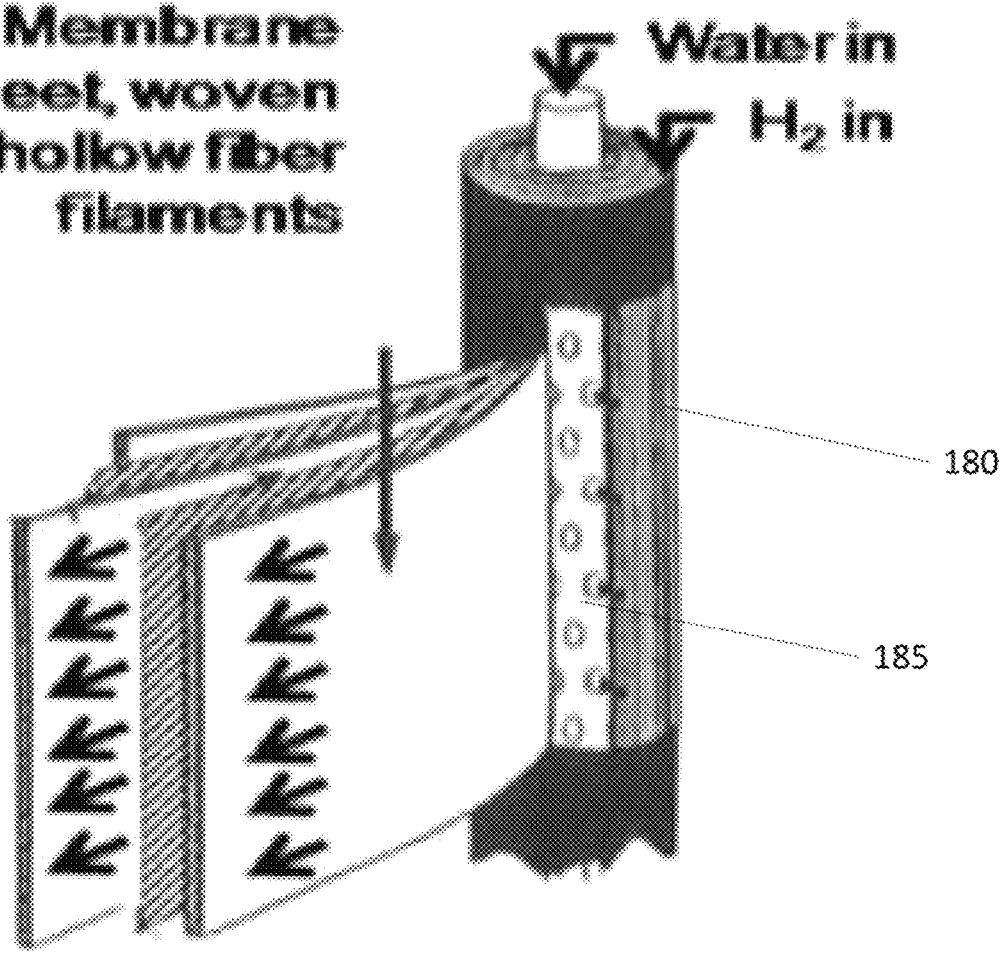
FIG. 6 illustrates a schematic of a sheet comprising a woven hollow fiber membrane with a partial cutaway and unwrapping to illustrate the layers of woven membrane sheets.

In various embodiments, with reference to FIG. 6, MBfR can comprise a membrane sheet 180 comprising a plurality of hollow fiber filaments woven into sheet 180 and wrapped around a perforated core 185 and an aqueous medium flows out radially. The lumen of each hollow fiber can be pressured with a gaseous feedstock for diffusion across the membrane wall.

To facilitate efficient generation of organic products, flux rates of gaseous feedstock can be varied through the selection of the membrane material, thickness, and area; the gas pressure within the lumen of the membrane, and the temperature of the reactor. For example, $H_2$ fluxes in an MBfR have been shown to depend on the fiber material and $H_2$ pressure in the lumen of the fiber: composite (2.75 g of $H_2$ per $m^2$ per day at 2 bar), polypropylene (0.64 g of $H_2$ per $m^2$ per day at 3 bar), and polyester (0.31 g of $H_2$ per $m^2$ per day at 3.3 bar) at 25° C. (Tang et al, 2012). Note that these are not the maximum fluxes possible, as these measurements are made under non-limiting conditions. Fluxes are inversely proportional to the pressure in the lumen of the membrane and directly proportional to the diffusion coefficient and increases with temperature.

In order to maintain a productive MBfR, the composition of the gas supply may be varied. Varying the gas supply can be useful for pH adjustment, for promotion of certain metabolic reaction pathways, or for promoting selective enrichment of desired microorganisms to inhibit undesired microorganisms. For example, gaseous substrates such as $H_2$ and $CO_2$ are consumed through autotrophic microbial reactions such as methanogenesis and homoacetogenesis, as shown below:

$$HCO_3^- + 4H_2 + H^+ \rightarrow 4CH_4 + 3H_2O \quad (6)$$

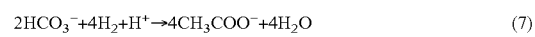
$$2HCO_3^- + 4H_2 + H^+ \rightarrow 4CH_3COO^- + 4H_2O \quad (7)$$

As demonstrated above, for the same amount of bicarbonate, methanogenesis consumes twice as many protons as homoacetogenesis and raises the reactor pH more significantly than homoacetogens, thereby affecting the microbes and the corresponding volumetric production rates. Nonetheless, pH can be managed in the MBfR biofilms by alternating the gas supply in the fibers between the preferred gaseous substrates and 100% $N_2$ gas, which enables the pH to re-adjust. Moreover, effective community management can be achieved by altering the gas mix to include CO, which promotes selective enrichment of desired partners that produce chemicals that inhibit methanogens. Specifically, CO has an inhibitory effect (only 50% of optimum growth) on methanogens (at headspace pressure of 0.4 atm) and sulfate reducers (at headspace pressure of 0.2 atm), while favoring optimal growth of acetogens at 1-2 atm headspace pressure of CO (See Sipma et al., 2006; Van Houten et al., 1996). Another example for varying the gaseous substrate includes supply of $CO_2$ or $NH_3$ gas to add the required acidity or alkalinity or C/N source, or both.

In various embodiments, the MBfR can be configured to operate at higher temperatures (e.g., 50-70° C. or more specifically, 55-60° C.) to grow thermophilic microorganisms with sustained or even higher gas delivery fluxes. In addition, higher temperature further maximizes the liquid-gas transfer rate in an MBfR due to lower viscosity of the gas, although the gas is less soluble in this temperature range. However, since the gas is fed directly to the biofilm in an MBfR, the solubility is less important that the liquid-gas transfer rate, and a higher temperature increases the reaction rate. Moreover, the production of ethanol at higher temperature reduces the distillation overhead by a considerable amount than what occurs in the mesophilic temperature ranges. For an ethanol titer of 7% by wt, the typical distillation energy input is estimated to be 19,000 MJ/ton of ethanol. Aqueous ethanol volatilizes at a significantly higher rate above 50° C., facilitating membrane assisted vapor stripping or vacuum/continuous distillation, as opposed to conventional distillation, which results in significantly lower energy requirements.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present membrane biofilm reactor, system, and method is not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

US Energy Information Administration, Annual Energy Outlook 2012 with projections to 2035. DOE-EIA-0383.

Munasinghe, P. C., Khanal, S. K. Biomass-derived syngas fermentation into biofuels: Opportunities and challenges. 2010. *Biores Technol.* 101(13): 5013-5022.

Latif, H., Zeidan, A. A., Nielsen, T. A., Zengler, K. Trash to treasure: production of biofuels and commodity chemicals via syngas fermenting microorganisms. Current. Op. *Biotechnol.* 27: 79-87.

Drake, H. L. Acetogenesis. 1994. Chapman & Hall Microbiology series. Springer, I edition.

Vega, J. L.; Antorrena, G. M.; Clausen, E. C.; Gaddy, J. L. Study of Gaseous Substrate Fermentations: Carbon Monoxide Conversion to Acetate. 2. Continuous Culture. *Biotechnol. Bioeng.* 1989, 34, 785-793.

Quereshi, N., Annous, B. M., Ezeji, T. A., Karcher, P., Maddox, I. 2005. Biofilm reactors for industrial bioconversion processes: employing potential of enhanced reaction rates. *Microb. Cell Factories* 4:24

Sipma, J., Lens, P. N. L., Stams, A. J. M., and Lettinga, G. (2006) Carbon monoxide conversion by anaerobic bioreactor sludges. FEMS Microbial Ecology. 44: 271-277.

Van Houten, R. T., van der Spoel, H., van Aelst, A. C., Hulshoff Pol, L. W. and Lettinga, G. (1996) Biological sulphate reduction using synthesis gas as energy and carbon source. *Biotechnol. Bioeng.* 50, 136-144.

Tang, Y., Zhou, C., Van Ginkel, S. W., Ontiveros-Valencia, A., Shin, J., Rittmann, B. E. Hydrogen permeability of the hollow fibers used in H2-based membrane biofilm reactors. 2012. *J Membr. Sci.* 407-408: 176-183.

Chung, J., Krajmalnik-Brown, R., Rittmann, B. E. Bioreduction of trichloroethene using a hydrogen-based membrane biofilm reactor. 2008. *Environ. Sci. Technol.* 42(2): 477 483.

Ziv-El, M. C., Popat, S. C., Cai, K., Halden, R. U., Krajmalnik-Brown, R., Rittmann, B. E. Managing methanogens and homoacetogens to promote reductive dechlorination of trichloroethene with direct delivery of H2 in a membrane biofilm reactor. 2012. *Biotechnol. Bioeng.* 109(9): 2200-2210.

Perez, J. M., Richter, H., Loftus, S. E., Angenent, L. T. Biocatalytic reduction of short-chain carboxylic acids into their corresponding alcohols with syngas fermentation. 2013. *Biotechnol. Bioeng.* 110(4): 1066-1077.

Vane, L. M., Alvarez, F. R. Membrane-assisted vapor stripping: energy efficient hybrid distillation-vapor permeation process for alcohol-water separation. 2008. *J Chem Bioechem Technol* 83(9): 1275-1287.

Tang, Y., C. Zhou, S. Van Ginkel, A. Ontiveros, J. Shin, and B. E. Rittmann (2012d). Hydrogen-permeabilities of the fibers used in a H2-based membrane biofilm reactor. J. Membrane Sci. 407-408: 176-183

Rittmann, B. E. and P. L. McCarty (2001). Environmental Biotechnology: Principles and Applications. McGraw-Hill Book Co., New York Merkey, B. V., B. E. Rittmann, and D. L. Chopp (2009). Modeling how soluble microbial products (SMP) support heterotrophs in autotroph-based biofilms. J. Theor. Biol. 259: 670-683

The invention claimed is:

1. A method of producing and extracting at least one of an alkane, an organic acid, or an alcohol comprising:
   providing a gas feedstock composition to at least one hollow fiber membrane of a membrane biofilm reactor, the gas feedstock composition alternating between a primary composition and a secondary composition, the membrane biofilm reactor comprising a biofilm disposed on the hollow fiber membrane in an aqueous medium; and
   extracting at least one of an alkane, an organic acid, or an alcohol from the aqueous medium;
   wherein the primary composition comprises $CH_4$ and the secondary composition comprises $CH_4$ and CO.

2. The method of claim 1, wherein the primary composition comprises a C-1 substrate and the secondary composition comprises one of $N_2$, $CO_2$, or 100% $NH_3$.

3. The method of claim 2, wherein the secondary composition comprises $CH_4$, CO, and $N_2$.

4. The method of claim 2, wherein the secondary composition comprises $CH_4$, CO, and $CO_2$.

5. The method of claim 2, wherein the secondary composition comprises $CH_4$, CO, and $NH_3$.

6. The method of claim 1, wherein the primary composition comprises 5-15:5-15:70-90 of $CH_4$, $O_2$, and $N_2$.

7. The method of claim 1, wherein the secondary composition comprises $O_2$.

8. The method of claim 1, wherein the gas feedstock composition alternates between the primary composition and the secondary composition for pH adjustment of the aqueous medium.

9. The method of claim 1, wherein the primary composition and the secondary composition are both below a lower flammability limit.

10. The method of claim 1, wherein the primary composition is different from the secondary composition.

11. The method of claim 1, wherein the primary composition further comprises $O_2$ and $N_2$, and is substantially non-combustible.

12. The method of claim 1, wherein the biofilm consists essentially of thermophilic microorganisms.

13. The method of claim 1, wherein the biofilm comprises at least a majority of at least one of the following microorganisms: methanotrophs, and *Methanosarcina acetivorans*.

14. The method of claim 1, wherein the aqueous medium has a temperature of 50° C. to 70° C.

* * * * *